United States Patent [19]

Bonse

[11] 4,436,905

[45] Mar. 13, 1984

[54] PREPARATION OF 4-METHYL-5-OXO-3-THIOXO-TETRAHYDRO-1,2,4,-(2H,4H)-TRIAZINES

[75] Inventor: Gerhard Bonse, Wuppertal-Elberfeld, Fed. Rep. of Germany

[73] Assignee: Bayer Aktiengesellschaft, Leverkusen, Fed. Rep. of Germany

[21] Appl. No.: 406,679

[22] Filed: Aug. 9, 1982

[30] Foreign Application Priority Data

Aug. 29, 1981 [DE] Fed. Rep. of Germany ....... 3134230

[51] Int. Cl.³ .......................................... C07D 253/06
[52] U.S. Cl. ................................................... 544/182
[58] Field of Search ........................................ 544/182

[56] References Cited

U.S. PATENT DOCUMENTS

| | | | |
|---|---|---|---|
| 3,544,570 | 12/1970 | Timmler et al. | 260/248 |
| 4,315,094 | 2/1982 | Bonse et al. | 544/182 |
| 4,328,340 | 5/1982 | Bonse et al. | 544/182 |

FOREIGN PATENT DOCUMENTS

| | | |
|---|---|---|
| 15452 | 9/1980 | European Pat. Off. |
| 35706 | 9/1981 | European Pat. Off. |
| 35708 | 9/1981 | European Pat. Off. |
| 1670912 | 3/1971 | Fed. Rep. of Germany |

Primary Examiner—John M. Ford

Attorney, Agent, or Firm—Sprung, Horn, Kramer & Woods

[57] ABSTRACT

4-Methyl-5-oxo-3-thioxo-tetrahydro-1,2,4-(2H,4H)-triazines, which are intermediate products for known herbicides, can be prepared in high yields by a process in which an acyl cyanide of the general formula $$R—CO—CN \qquad (II)$$

wherein R represents an optionally substituted aliphatic radical having up to 12 carbon atoms, an optionally substituted cycloalkyl radical having 3 to 10 carbon atoms, an optionally substituted phenyl or naphthyl radical or an optionally substituted heterocyclic radical, is reacted with a carboxylic acid anhydride of the general formula $$R^1—CO—O—CO—R^1 \qquad (II)$$

in which $R^1$ represents an optionally substituted aliphatic radical having up to 8 carbon atoms or an optionally substituted phenyl radical, in the presence of a strong acid and, if appropriate, in the presence of a solvent, at a temperature between $-50°$ and $150°$ C., and the reaction mixture thus obtained is then reacted directly with 4-methyl-thiosemicarbazide ($CH_3—NH—CS—NH—NH_2$).

19 Claims, No Drawings

PREPARATION OF 4-METHYL-5-OXO-3-THIOXO-TETRAHYDRO-1,2,4,-(2H,4H)-TRIAZINES

The present invention relates to an unobvious process for the preparation of certain largely known 6-substituted 4-methyl-5-oxo-3-thioxo-tetrahydro-1,2,4-(2H 4H)-triazines.

The triazine produced by the process of the present invention can be used as intermediate products for the synthesis of known herbicidal 1,2,4-triazin-5(4H)-ones.

A number of processes have been disclosed for the preparation of 6-substituted 4-methyl-5-oxo-3-thioxo-tetrahydro-1,2,4-(2H, 4H)-triazines.

Using α-ketocarboxylic acids or the salts thereof as starting materials, such triazines can be prepared in yields of 80% of theory by boiling in water for several hours, up to 10 hours, with 4-methyl-thiosemicarbazide (see "Fortschritte der chemischen Forschung" ("Progress in Chemical Research") Volume 5, pages 189 (1965); DE-OS (German Published Specification) No. 1,670,912; and DE-OS (German Published Specification) No. 2,938,384).

According to DE-OS (German Published Specification) No. 2,908,964, such triazines can furthermore be prepared by condensation of 2-mercapto-2-cyclohexylidene-acetic acid with 4-methyl-thiosemicarbazide. 2-Mercapto-2-cyclohexylideneacetic acid is obtained from cyclohexanone and N-methylrhodenine by alkaline hydrolysis of the condensation product cyclohexylidene-N-methylrhodanine.

The multi-stage, previously known processes, mentioned have the disadvantage that many of the α-ketocarboxylic acids required as starting materials can only be obtained with difficulty. Some of them have to be prepared in several stages by methods which are industrially extremely expensive and give only unsatisfactory yields in some cases (see the review article: Synthesis routes to α-ketocarboxylic acids in "Comprehensive Organic Chemistry" Volume 2, 779 (1979).

The present invention now provides a process for the production of 4-methyl-5-oxo-3-thioxo-tetrahydro-1,2,4-(2H, 4H)-triazine of the following general formula (I) which can occur in the two tautomeric forms (Ia) and (Ib).

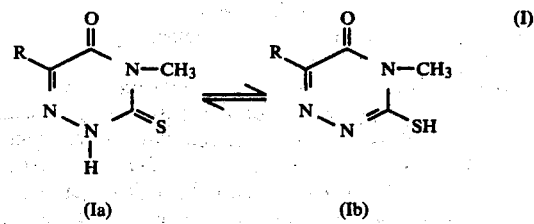

wherein R represents an optionally substituted aliphatic radical having up to 12 carbon atoms, an optionally substituted cycloalkyl radical having 3 to 10 carbon atoms, an optionally substituted phenyl or naphthyl radical or an optionally substituted heterocyclic radical.
characterized in that an acyl cyanide of the general formula $$R-CO-CN \quad (II)$$

in which R has the meaning given above, is reacted with a carboxylic acid anhydride of the general formula $$R^1-CO-O-CO-R^1 \quad (III)$$

in which $R^1$ represents an optionally substituted aliphatic radical having up to 8 carbon atoms or an optionally substituted phenyl radical,
in the presence of a strong acid and, if appropriate, in the presence of a solvent, at a temperature between −50° and 150° C., and the reaction mixture thus obtained is then reacted directly with 4-methyl-thiosemicarbazide ($CH_3-NH-CS-NH-NH_2$).

The process of the present invention allows compound of formula (I) to be obtained in a surprisingly simple manner in a high yield and in high purity.

The triazines of the formula (I) thus obtained can subsequently be converted into the herbicidal 6-alkyl (aryl)-3-dimethylamino-4-methyl-1,2,4-triazin-5-(4H)-ones according to known methods (see German Published Specifications DOS No. 1,670,912, 2,908,983, 2,908,964, 2,938,384 and U.S. application Ser. No. 229,919, filed Sept. 8, 1981, now pending.

The process according to the present invention comprises a procedure which, compared with the prior art, is absolutely novel and advantageous and in which it is possible for the first time, in a surprisingly smooth and uniform course of reaction, to convert acyl cyanides directly into extraordinarily pure 4-methyl-5-oxo-3-thioxotetrahydro-1,2,4-(2H, 4H)-triazines (I) in almost quantitative yield, under mild conditions in a "one-pot process", without having to isolate any intermediate products.

The process according to the invention avoids the previously mentioned disadvantages associated with the comparable previously known processes; this implies a very substantial industrial simplification.

If pivaloyl cyanide is used as the acyl cyanide of the general formula (II) and acetic acid anhydride is used as the carboxylic acid anhydride of the gneral formula (III) and concentrated sulphuric acid is used as the strong acid, the course of the reaction according to the present invention is illustrated by the following equation:

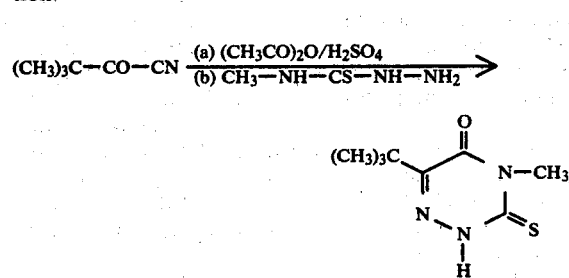

Preferred acyl cyanides of formula (II) to be employed as starting materials are those in which
R represents a straight-chain or branched alkyl radical having 1 to 4 carbon atoms which is optionally substituted by a substituent selected from alkoxy having 1 to 4 carbon atoms, carbalkoxy having 1 to 4 carbon atoms in the alkoxy group, nitro, cyano and halogen (such as fluorine, chlorine, bromine or iodine), represents a cycloalkyl radical which has 3 to 6 carbon atoms in the ring system and is optionally substituted by a substituent selected from alkyl, alkoxy or carbalkoxy each having up to 4 carbon atoms, nitro, cyano and halogen (such as fluorine, chlorine and bromine), represents a naphthyl or phenyl radical which is optionally substituted by a substituent selected from alkyl, alkoxy or carbalkoxy each having up to 4 carbon atoms, nitro and halogen (such as fluorine, chlorine and bromine), or represents a 5-membered or 6-membered heterocyclic radical which can contain 1 to 3 hetero-atoms (such as oxygen, sulphur and/or nitrogen) in the ring and in addition can be fused to a benzene ring, and which is optionally substituted by a substituent selected from alkyl, alkoxy or carbalkoxy each having up to 4 carbon atoms, nitro, cyano and halogen (such as, for example, fluorine, chlorine and bromine).

The following may be mentioned as examples of particularly suitable heterocyclic radicals for radical R: morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

Acyl cyanides of the formula (II) are known and can be prepared in a simple manner by known processes (see Angew. Chem. 68, pages 425–435 (1975); and also German Published Specifications 2,614,240, 2,708,182 and 2,708,183, German Patent Specification 2,660,344 and U.S. Pat. Nos. 4,238,412 and 4,143,068. Pivaloyl cyanide may be mentioned as an acyl cyanide of formula (II) which is particularly preferred within the scope of this invention.

Preferred carboxylic acid anhydrides of formula (III) furthermore to be employed as starting materials are those in which $R^1$ represents an optionally chlorine-substituted alkyl radical having 1 to 4 carbon atoms, or a phenyl radical.

Carboxylic acid anhydrides of the formula (III) are available industrially on a large scale, and can be prepared, for example from the corresponding carboxylic acids, according to generally known methods.

Propionic acid anhydride, the anhydrides of the chloroacetic acids and, especially, acetic acid anhydride are carboxylic acid anhydride which are particularly preferred anhydrides of formula (III) within the scope of this invention.

The reaction according to the invention is carried out in the presence of a strong acid. Suitable acids of this type are inorganic acids, such as concentrated sulphuric acid, hydrohalic acids (for example anhydrous hydrogen chloride and hydrogen bromide), nitric acid, perchloric acid and phosphoric acid, and also Lewis acids, such as boron trifluoride, aluminum chloride or zinc chloride. Aliphatic and aromatic sulphonic acid phosphonic acids and halogenoalkanecarboxylic acids (for example, trichloroacetic acid) are furthermore suitable. Oxo acids, in particular concentrated sulphuric acid, are preferably used.

It is possible to carry out the reaction according to the invention in the presence of one or more acids of this type.

The reaction temperatures can be varied within the stated relatively wide range. That is to say, the reaction is carried out, as given above, at a temperature between $-50°$ and $+150°$ C., preferably between $0°$ and $100°$ C., in particular between $50°$ and $90°$ C.

The reaction is carried out in general under normal pressure.

The reaction can be carried out in the absence or in the presence of a solvent or solubilizer. Certain organic solvents are suitable as the solubilizer; glacial acetic acid, dichloromethane, dialkyl ethers (such as diethyl ether or di-isopropyl ether) and diaryl ethers (such as diphenyl ether) are particularly suitable.

In carrying out the process according to the invention, in general from 0.5 to 6 mols, preferably from 0.8 to 4 mols of carboxylic acid anhydride of the formula (III) are employed per mol of acyl cyanide of the formula (II); a molar ratio of acyl cyanide (II) to carboxylic acid anhydride (III) of 1:1 to 1:2 is particularly preferred.

The acids required for carrying out the process according to the invention are employed in from catalytic amounts to amounts greater than the stoichiometric amount. In general from 0.5 to 10 mols preferably from 0.8 to 8 mols particularly preferably from 1 to 4 mols of acid are employed per mol of acyl cyanide (II).

A molar ratio of carboxylic acid anhydride (III) to the strong acid of 1:2 is particularly advantageous.

Furthermore, it is particularly advantageous to employ the acyl cyanide (II) and 4-methylthiosemicarbazide in equimolar amounts.

It is thus particularly advantageous in carrying out the process according to the invention to react acyl cyanide (II), carboxylic acid anhydride (III), the strong acid and 4-methyl-thiosemicarbazide in the molar ratio of from 1:1:2:1 to 1:2:4:1.

When the process is carried out on an industrial scale, it can, however, be advantageous, while keeping the molar ratio of the carboxylic acid anhydride (III) to the strong acid constant at 1:2, to employ an excess of these two components in order to maintain the resulting reaction mixture in a readily stirrable form.

The following procedure is advantageously employed in carrying out the process according to the invention:

The strong acid or a mixture of the solvent and the strong acid is initially introduced, and the carboxylic acid anhydride of formula (III) and the acyl cyanide of formula (II) are added successively; the reaction mixture thus obtained is introduced, either immediately after the end of the addition of the acyl cyanide or after being further stirred for a certain time (a maximum of 3 hours), into an aqueous solution preferably containing mineral acid, or an aqueous-alcoholic solution, or into an aqueous suspension of 4-methyl-thiosemicarbazide. It is also possible to introduce conversely to introduce the 4-methyl-thiosemicarbazide solution or suspension into the previously mentioned reaction mixture.

The reaction mixture thus obtained is then rendered approximately weakly acidic to neutral by the addition of bases, and is warmed.

Any of the inorganic basic compounds which can customarily be used as acid-binding agents can in principle be employed as bases. These include, as preferences, alkali metal and alkaline earth metal oxides, hydroxides, carbonates and bicarbonates, the following metals being preferred: sodium, potassium and calcium; and tertiary amines (such as trimethylamine, triethylamine, pyridine, lauryldimethylamine, stearyldimethylamine, N,N-diethylcyclohexylamine, N-ethylpiperidine, N-methylpyrrolidine, $\alpha$-, $\beta$- and $\gamma$-picoline, N-propylpiperidine, quinoline, isoquinoline, quinoxaline, tri-n-amylamine, tri-n-propylamine or N,N-dimethylbenzylamine).

The reaction times are in general from 1 to 3 hours. The reaction product is precipitated as a rule in crystalline form, and can be isolated in a customary manner by filtration or by extraction.

Suitable extracting agents for this purpose are solvents which are not completely miscible with water, for example ethers (such as diethyl ether or diisopropyl ether), esters (such as ethyl acetate), ketones (such as methyl isobutyl ketone), halogenohydrocarbons (such as dichloromethane, chlorobenzene or dichlorobenzene) and aromatic compounds, (such as benzene, toluene, o-xylene, ethylbenzene, cumene or nitrobenzene). Dichloromethane is preferably used.

The triazines of formula (I) obtained by the process according to the invention can be alkylated in a known manner by reaction with a $C_1$–$C_6$ alkyl halide (such as methyl bromide) in the presence of a base (such as sodium hydroxide) in aqueous solution, at temperatures between 0° and 50° C., to give 3-alkylthiotriazinones of the formula (IV). The 6-alkyl(aryl)-3-dimethyl-amino-4-methyl-1,2,4-triazin-5-(4H)-ones of formula (V) which are known to be herbicidal are then obtained from these compounds by reaction with dimethylamine in the presence of aliphatic carboxylic acids and an organic sulpho acid (see German Published Specifications DOS Nos. 1,670,912, 2,908,963, 2,908,964 and 2,938,384).

The course of this subsequent reaction may be illustrated by the following equation:

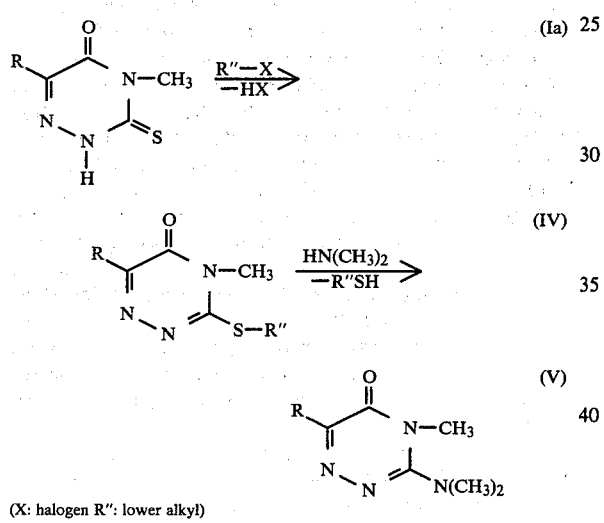

(X: halogen R″: lower alkyl)

The examples which follow are intended merely to illustrate the process of the present invention.

PREPARATIVE EXAMPLES

Example 1

6-tert.-Butyl-4-methyl-5-oxo-3-thioxo-tetrahydro-1,2,4-(2H, 4H)-triazine

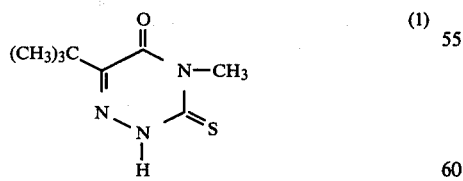

(1)

First 51.2 g (0.5 mol) of acetic acid anhydride and then 27.8 g (0.25 mol) of pivaloyl cyanide were introduced, in each case at room temperature, into 98.0 g (1.0 mol) of initially introduced concentrated sulphuric acid. After this reaction mixture has been stirred for a further hour at 40° C., it was stirred into a solution of 23.3 g (0.25 mol) of 4-methyl-thiosemicarbazide in 200 ml of 1 N HCl. After the end of the addition, the mixture was stirred for a further hour at room temperature. The pH value was then adjusted to about 5 with 1,200 ml of 2 N NaOH, and the mixture was warmed to 80° C. for one hour. After the mixture had cooled, the precipitated reaction product was filtered off under suction, washed with 200 ml of water and dried. 45.8 g (92% of theory) of 6-tert.-butyl-4-methyl-5-oxo-3-thioxo-tetrahydro-1,2,4-(2H, 4H)-triazine were obtained as colorless crystals of melting point 214° C.; purity according to gas chromatographic determination >99%. For subsequent reactions, no further purification operations were required.

The following compounds of the general formula I

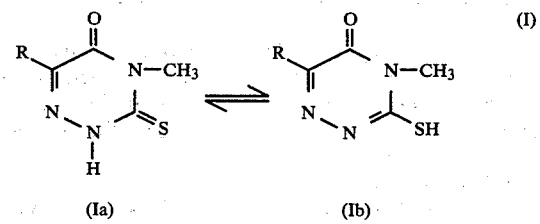

could be prepared in a corresponding manner:

TABLE 1

| Compound No. | R | Melting point (°C.) |
|---|---|---|
| 2 | —CH₃ | 186 |
| 3 | —CH(CH₃)₂ | 191 |
| 4 | —CH₂CH(CH₃)₂ | 135 |
| 5 | —CH(CH₃)C₂H₅ | 117 |
| 6 | —CH₂C(CH₃)₃ | 171 |
| 7 | cyclopentyl-H | 194 |
| 8 | cyclohexyl-H | 189 |
| 9 | —CH₂—phenyl | 184 |
| 10 | phenyl | 223 |
| 11 | —C₆H₄—NO₂ | 260 |
| 12 | —C₆H₄—OCF₃ | 198 |
| 13 | —C₆H₄—F | 217 |

TABLE 1-continued

| Compound No. | R | Melting point (°C.) |
|---|---|---|
| 14 | 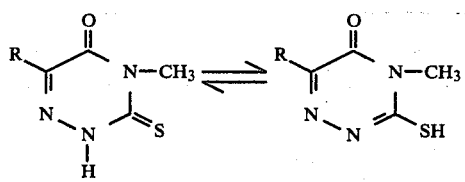 | 210 |
| 15 | | 247 |

It will be understood that the specification and examples are illustrative but not limitative of the present invention and that other embodiments within the spirit and scope of the invention will suggest themselves to those skilled in the art.

What is claimed:

1. A process for the production of a 4-methyl-5-oxo-3-thioxo-tetrahydro-1,2,4-(2H, 4H)-triazine of the two tautomeric forms

wherein R is an optionally substituted aliphatic radical having up to 12 carbons atoms, an optionally substituted cycloalkyl radical having 3 to 10 carbon atoms, an optionally substituted phenyl or naphthyl radical or an optionally substituted heterocyclic radical,
comprising in a first step reacting an acyl cyanide of the formula

R—CO—CN with a carboxylic acid anhydride of the formula

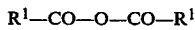

in which R¹ is an optionally substituted aliphatic radical having up to 8 carbon atoms or an optionally substituted phenyl radical,
in the presence of a strong acid at a temperature between about −50° and 150° C., and in a second step contacting the reaction mixture thus obtained directly with 4-methylthiosemicarbazide.

2. A process according to claim 1, wherein the first step is carried out in the presence of a solvent.

3. A process according to claim 1, wherein the first step is carried out at a temperature between about 0° and 100° C.

4. A process according to claim 1, wherein the first step is carried out at a temperature between about 50° and 90° C.

5. A process according to claim 1, wherein the molar ratio of acyl cyanide to carboxylic acid anhydride is from about 1:0.5 to 1:6.

6. A process according to claim 1, wherein the molar ratio of acyl cyanide to carboxylic acid anhydride is from about 1:0.8 to 1:4.

7. A process according to claim 1, wherein the molar ratio of acyl cyanide to carboxylic acid anhydride is from about 1:1 to 1:2.

8. A process according to claim 1, wherein the molar ratio of acyl cyanide to strong acid is from about 1:0.5 to 1:10.

9. A process according to claim 1, wherein the molar ratio of acyl cyanide to strong acid is from about 1:0.8 to 1:8.

10. A process according to claim 1, wherein the molar ratio of acyl cyanide to strong acid is from about 1:1 to 1:4.

11. A process according to claim 1, wherein the molar ratio of carboxylic acid anhydride to strong acid is about 1:2.

12. A process according to claim 1, wherein the molar ratio of acyl cyanide to carboxylic acid anhydride to stronf acid to 4-methyl-thiosemicarbazide is from about 1:1:2:1 to 1:2:4:1.

13. A process according to claim 1, which R is an alkyl radical having 1 to 4 carbon atoms which is optionally substituted by a substituent selected from alkoxy having 1 to 4 carbon atoms, carbalkoxy having 1 to 4 carbon atoms in the alkoxy group, nitro, cyano and halogen; a cycloalkyl radical which has 3to 6 carbon atoms in the ring system and is optionally substituted by a substitutent selected from alkyl, alkoxy, or carbalkoxy each having up to 4 carbon atoms, nitro, cyano and halogen; a naphthyl or phenyl radical which is optionally substituted by a substitutent selected from alkyl, alkoxy or carbalkoxy each having up to 4 carbon atoms, nitro and halogen; a 5-membered or 6-membered hetero-cyclic radical which can contain 1 to 3 hetero-atoms in the ring, and which is optionally substituted by a substituent selected from alkyl, alkoxy or carbalkoxy each having up to 4 carbon atoms, nitro, cyano and halogen.

14. A process according to claim 1, wherein the acyl cyanide is pivaloyl cyanide.

15. A process according to claim 1, wherein R' is an optionally chlorine-substituted alkyl radical having 1 to 4 carbon atoms, or a phenyl radical.

16. A process according to claim 1, wherein the acid anhydride is acetic acid anhydride.

17. A process according to claim 1, wherein the stong acid is concentrated sulphuric acid.

18. A process according to claim 12, wherein the acyl cyanie is pivaloyl cyanide, the acid anhydride is acetic acid anhydride, the strong acid is concentrated sulphuric acid, and the first step is carried out at a temperature between about 50° and 90° C.

19. In the preparation of a compound of the formula

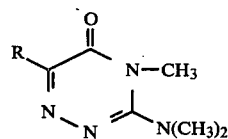

in which R is an optionally substituted aliphatic radical having up to 12 carbon atoms, an optionally substituted cycloalkyl radical having 3 to 10 carbon atoms, an optionally substituted phenyl or napthyl radical or an optionally substituted heterocyclic radical, by preparing a 4-methyl-5-oxo-3-thioxo-tetrahydro-1,2,4-(2H,4H)-triazine of the two tautomeric forms

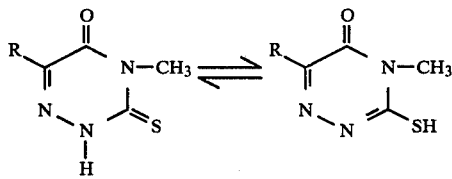

reacting the triazine with an alkylating agent and then with dimethylamine, the improvement which comprises preparing the triazine according to claim 1 and then directly reacting the triazine with the alkylating agent without purification.

* * * * *